United States Patent

Ibe

[11] Patent Number: 6,049,422
[45] Date of Patent: Apr. 11, 2000

[54] OPTICAL SYSTEM FOR NON-FLEXIBLE ENDOSCOPES

[75] Inventor: Hiroshi Ibe, Hachioji, Japan

[73] Assignee: Olympus Optical Co., Ltd., Tokyo, Japan

[21] Appl. No.: 09/276,506

[22] Filed: Mar. 25, 1999

[30] Foreign Application Priority Data

Mar. 26, 1998 [JP] Japan .................................. 10-096983

[51] Int. Cl.$^7$ ............................ G02B 23/00; A61B 1/002
[52] U.S. Cl. ......................... 359/434; 359/362; 359/663; 600/160
[58] Field of Search ........................... 359/362, 434–435, 359/663, 682, 753; 600/160–161, 167, 170–172, 130, 138, 101, 105, 135

[56] References Cited

U.S. PATENT DOCUMENTS

| 5,603,687 | 2/1997 | Hori et al. ............................... 600/166 |
| 5,632,718 | 5/1997 | Igarashi et al. ......................... 600/160 |
| 5,891,015 | 4/1999 | Strahle ..................................... 359/434 |

FOREIGN PATENT DOCUMENTS 7-325249   12/1995   Japan .

Primary Examiner—Thong Nguyen
Attorney, Agent, or Firm—Pillsbury Madison & Sutro LLP

[57] ABSTRACT

An optical system for non-flexible endoscopes comprising an illumination optical system and an observation optical system which are disposed in an insert section, wherein the observation optical system comprises, in order from a tip thereof, an objective optical system and a single cycle type relay optical system, and an outside diameter D1 of a lens component in the objective optical system whichever has a largest outside diameter, an outside diameter D2 of a lens component in the relay optical system whichever has a largest outside diameter and an outside diameter D3 of the insert section are in relationship expressed by the following conditions (1) and (2):

$$L/D1 < 20 \quad (1)$$

$$0.7 < D2/D3 < 0.9 \quad (2).$$

5 Claims, 5 Drawing Sheets

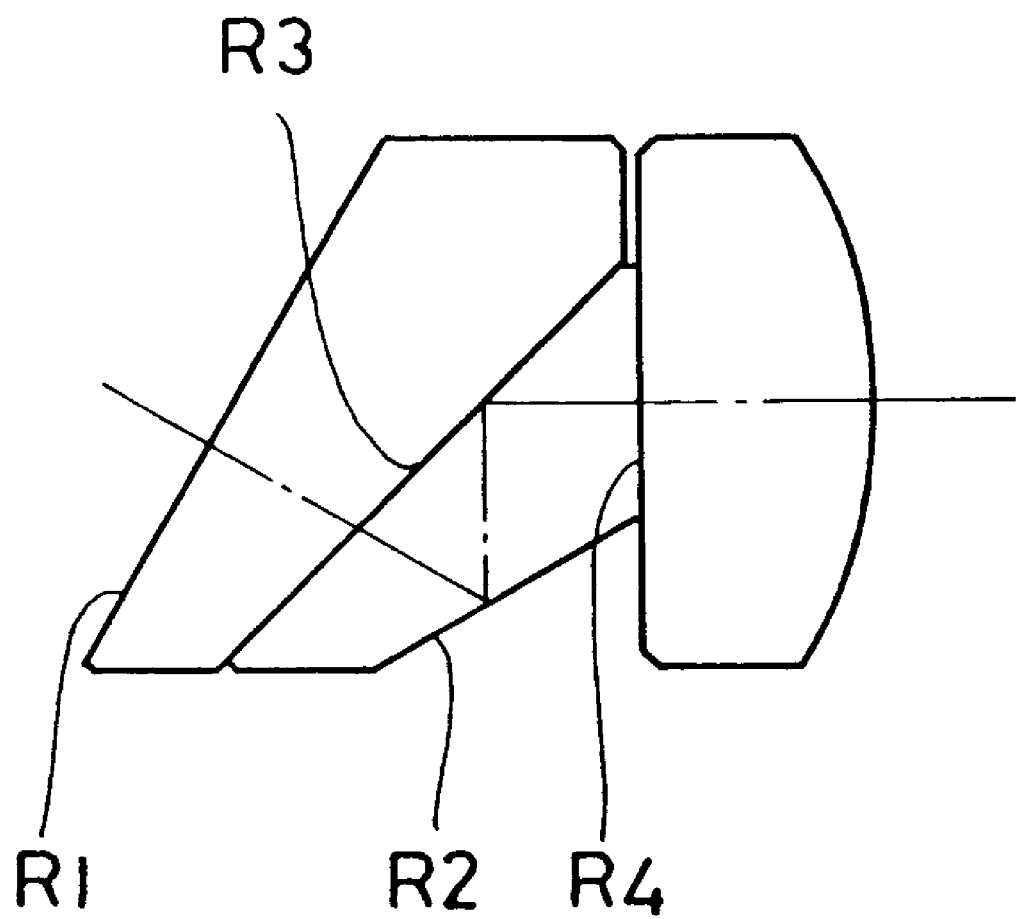

OPTICAL SYSTEM FOR NON-FLEXIBLE ENDOSCOPES

BACKGROUND OF THE INVENTION a) Field of the Invention

The present invention relates to an optical system for non-flexible endoscopes.

b) Description of the Prior Art

A non-flexible endoscopes has a composition shown in FIG. 1, for example, or consists of an elongated insert section 11 which is to be inserted into a cavity of a living body or the like, and a grip section 12 which is to be located outside the cavity in use of the endoscope and is held by an operator's hand or an endoscope holder. Furthermore, an illumination system 13 which illuminates an object, and an observation optical system 14 which is used for observing and picking up an image of the object are disposed within a range from the insert section to the grip section.

A section of the observation optical system 14 which is disposed in the insert section consists of an objective optical system 1 which forms a real image of the object and a relay optical system 2 which transfers the image of the object formed by the objective optical system 1 into the grip section 12. This relay optical system transfers the image ordinarily three cycles. Furthermore, a section of the observation optical system 14 which is disposed in the grip section 12 is an eyepiece optical system which makes the transferred object of the image visible by an eye.

When the non-flexible endoscope is used for a surgical operation under endoscopic observation, it is necessary to observe an image of an object on a screen of a TV monitor and a TV camera for the non-flexible endoscope is attached to an eyepiece mount of the grip section. A TV camera is indispensable in a surgical field for digestive system. Therefore, a TV camera 17 for the non-flexible endoscope which comprises an image pickup optical system 15 and a solid-state image pickup device 16 is attached as shown in FIG. 1. In FIG. 1, a reference numeral 18 represents a camera control unit and a reference numeral 19 designates a TV monitor.

The conventional non-flexible endoscope described above is configured to maintain brightness of the optical system by transmitting an image while relaying it a plurality of cycles on the order of three times.

A non-flexible endoscope which is used for surgical operations under endoscopic observation has an insert section which ordinarily has an outside diameter not larger than 10 mm and a length on the order of 300 mm or longer. In order to transfer an image while maintaining required brightness through an optical system of such an insert section, it is necessary to enlarge an NA of a relay optical system by increasing a number of relay cycles. When required brightness is maintained by such means, however, the relay optical system produces aberrations in large mounts, thereby degrading an image quality. When the number of relay cycles is increased, the relay optical system uses a larger number of lens components, requires a higher manufacturing cost, and degrades an image quality due to manufacturing errors.

As an optical system which is configured to transfer an image a single relay cycle in order to correct these defects, there is known an optical system disclosed by Japanese Patent Kokai Publication No. Hei 7-325249. This optical system for non-flexible endoscopes cannot be configured as an optical system which has a wide field and is compatible with a non-flexible endoscope for oblique observation.

Even when a relay optical system is configured to transfer an image while relaying it a plurality of cycles, it is general that aberrations are not aggravated so much on an image transferred through a relay optical system as a whole so far as aberrations are corrected sufficiently favorably in a relay optical system for a single relay cycle. In order to correct aberrations favorably in the optical system for single relay cycle, however, it is necessary to compose the relay optical system of a larger number of lens components. When the relay lens system is composed of a larger number of lens components, the optical system comprises a larger number of lens surfaces, and a light bundle is reflected and scattered more times by the larger number of lens surfaces, thereby lowering brightness and contrast of an image. Furthermore, the larger number of lens components enhance a manufacturing cost of the relay lens system and increase undesirable factors such as manufacturing errors at a manufacturing stage which degrades an image quality. For this reason, it is necessary that a single cycle type relay optical system must have a composition as simple as possible so that it comprises a reduced number of lens components. When the single cycle type relay optical system is composed of a reduced number of lens components, however, the optical system is incapable of correcting aberrations favorably. Since a relay optical system which transfers an image a plurality of time has factors which are conflicting with one another, it is difficult to configure an optical system which has a simple composition, can be manufactured at a low cost and corrects aberrations favorably.

When an image is relayed a large number of cycles, aberrations are multiplied by the number of relay cycles in a relay optical system as a whole. When an image is to be transferred by a relay optical system for a definite distance, a larger number of relay cycles shorten a length of an optical system for a single relay cycle and make it inevitable to strengthen a power of each surface of the relay optical system, whereby aberrations are produced in larger amounts per relay cycle. When a number of relay cycles in a relay optical system is multiplied by an integer, aberrations are produced in the relay optical system in amounts larger than those multiplied by the integer.

An optical system for non-flexible endoscopes is configured to correct aberrations produced in a relay optical system with an objective optical system and so on which are other than a relay optical system so that aberrations are corrected favorably in the optical system for non-flexible endoscopes as a whole. However, it is preferable to reduce aberrations as far as possible in a relay optical system since aberrations produced by the relay optical system cannot be corrected sufficiently favorably under conditions such as a restricted number of lens components and a restricted outside diameter.

When a relay optical system is configured for an increased number of relay cycles, it uses an increased number of lens components and an increased number of lens surfaces, whereby the relay optical system lowers brightness and contrast, enhances manufacturing cost of the optical system and degrades an image quality. In order to correct these defects, it is desirable to configure a relay optical system for a single relay cycle.

A technical theme for a relay optical system which transfers an image a single relay cycle lies in maintenance of brightness. When a number of relay cycles is reduced in a relay optical system which transfers an image for a definite distance, its numerical aperture is reduced and its brightness is lowered.

As a conventional example which solves this problem, there is known an optical system disclosed by Japanese Patent Publication No. Hei 7-325249. This conventional example is configured for a single relay cycle but maintains brightness sufficient for practical use by adopting a long objective optical system, a short relay optical system and an observation optical system having a large NA.

Since this conventional example uses the long objective optical system, however, it has a defect that it cannot have a wide field angle and is incompatible with non-flexible endoscopes for oblique observation.

An optical system for non-flexible endoscopes uses an objective optical system which is mostly of the retrofocus type since the objective optical system must have a small outside diameter and a wide field angle. When a total length of the retrofocus type objective optical system is prolonged with its outside diameter kept unchanged, rays coming from marginal portions of a visual field have small angle relative to an optical axis at a location of a pupil, thereby making it necessary to shorten a focal length of a front diversing lens component. When the focal length of the front diverging lens component is shortened too much, however, a remarkably complicated lens composition must be adopted to correct aberrations produced in large amounts by the front diverging lens component with other sections of an observation optical system. Since an observation optical system which is practically usable cannot have a complicated composition and is incapable of favorably correcting aberrations. Furthermore, when a focal length of a front diverging lens component is restricted due to correction of aberrations, it is impossible to configure an optical system which has a large field angle. The conventional example of optical systems for non-flexible endoscopes cannot have a field angle larger than 70° and it is preferable, when sufficiently favorable correction of aberrations is taken into consideration, that an optical system has a field angle not exceeding 60°.

Since a field angle larger than 70° is mostly desired for non-flexible endoscopes to be used for surgical operations under endoscopic observation, the conventional example of optical system described above cannot be used for these non-flexible endoscopes.

This conventional example can hardly have the required field angle as described above.

The conventional example of optical system can hardly have the required field angle as described above and has a pupil of the objective optical system which is located in the vicinity of a center of the objective lens system so that rays coming from marginal portions of a visual field have angles as large as possible relative to an optical axis at a location of the pupil of the objective optical system. Since the conventional objective optical system has a large total length and the pupil which is located in the vicinity of the center thereof, a distance between a tip of the objective optical system and the pupil thereof is longer than the optical system for non-flexible endoscopes. When this optical system is used to compose a non-flexible endoscope for oblique observation, rays are high on a visual field direction changing prism which is disposed on a side of a tip of the objective optical system and eclipsed, whereby eclipse at a location apart from the pupil undesirably darkens and ununiformalizes brightness of an image.

The conventional single relay cycle type optical system for non-flexible endoscopes has the defect that it cannot have a wide field angle and is incompatible with non-flexible endoscopes for oblique observation as described above.

SUMMARY OF THE INVENTION

A primary object of the present invention is to provide an optical system for non-flexible endoscope for oblique observation which uses a relay optical system having a single relay cycle, forms a high quality image, comprises a small number of lens components, has a wide field angle and is practically usable.

A non-flexible endoscope according to the present invention comprises an illumination optical system and an observation optical system which are disposed in an insert section: the observation optical system comprising, in order from a side of a tip thereof, at least an objective optical system and a single cycle type relay optical system, and satisfying conditions (1) and (2) shown below.

$$L/D1 < 20 \tag{1}$$

$$0.7 < D2/D3 < 0.9 \tag{2}$$

BRIEF DESCRIPTION OF THE DRAWINGS

FIG. 7 shows a sectional view illustrating a tip of a non-flexible endoscope comprising the optical system preferred as the second embodiment.

DETAILED DESCRIPTION OF THE PREFERRED EMBODIMENTS

The optical system for non-flexible endoscopes according to the present invention is characterized in that it comprises an illumination optical system and an observation optical system, and that the observation optical system which is to be disposed in an insert section comprises, in order from a tip thereof, at least an objective optical system and a relay optical system which relays single cycle, and satisfies the following conditions (1) and (2):

$$L/D1 < 20 \tag{1}$$

$$0.7 < D2/D3 < 0.9 \tag{2}$$

wherein the reference symbol L represents a distance as measured from a tip of the objective optical system to an image surface, the reference symbol D1 designates an outside diameter of a lens component in the objective optical system whichever has a largest outside diameter, the reference symbol D2 denotes an outside diameter on a lens component of the relay optical system whichever has a largest outside diameter and the reference symbol D3 represents an outside diameter of the insert section.

Figure 1:
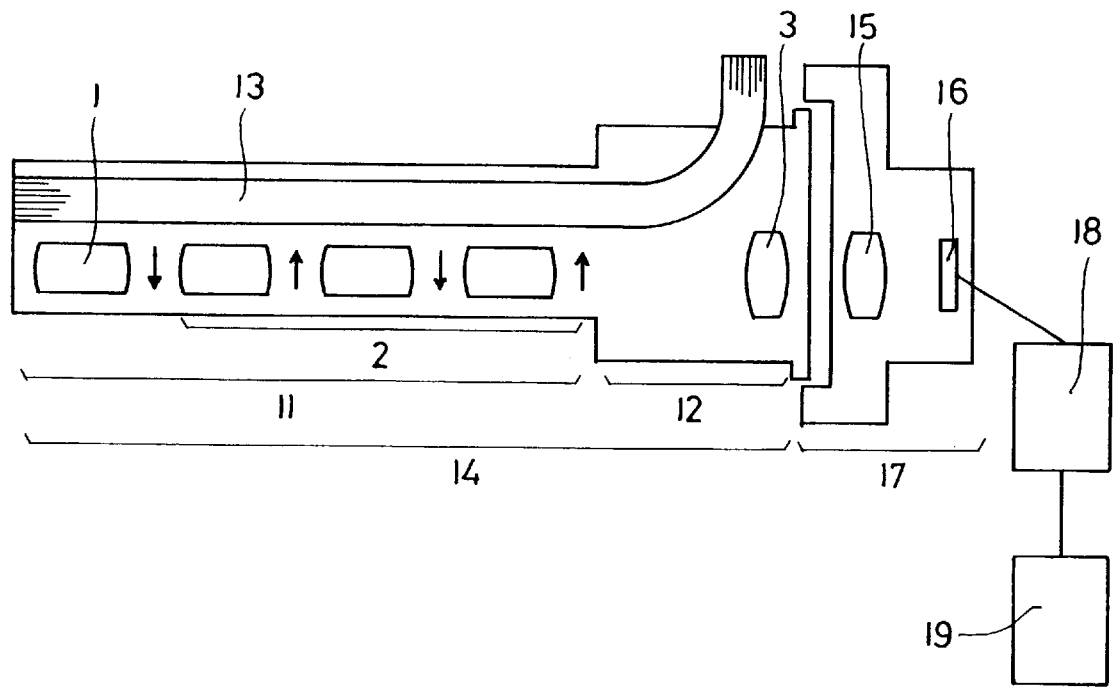
FIG. 1 shows a sectional view illustrating a composition of a conventional non-flexible endoscope.
Figure 2:
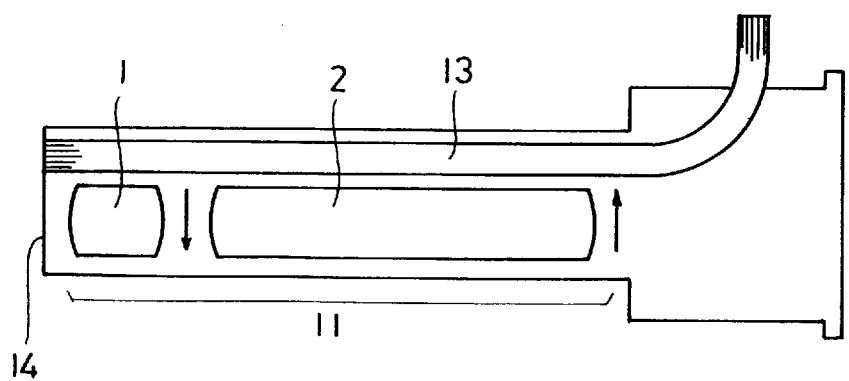
FIG. 2 shows a sectional view illustrating a foundamental composition of the non-flexible endoscope according to the present invention.

The optical system for non-flexible endoscopes according to the present invention has a composition shown in FIG. 2, for example, and has an elongated insert section 11 of a non-flexible endoscope which is to be inserted into a cavity of a living body or the like. Disposed in this insert section 11 are an illumination optical system 13 which illuminates an object in the cavity and an observation optical system 14 for observing the object in the cavity. This observation optical system 14 comprises, in order from the tip thereof, at least an objective lens component 1 which forms a real image of the object and a relay optical system 2 which transfers the image formed by the objective lens component 1 outside the insert section. The relay optical system 2 is configured to relay the image a single cycle.

In order to configure an optical system for non-flexible endoscopes so as to have a wide field angle, rays coming from marginal portions of a visual field must have large angles relative to an optical axis at a location of a pupil of an objective optical system since a focal length of a front diverging lens unit of the objective optical system is restricted due to correction of aberrations. In order to allow these rays to have large angles, it is necessary to shorten a total length of the objective optical system or locate the pupil of the objective optical system in the vicinity of the objective optical system.

In order to obtain a non-flexible endoscope for oblique observation which is practically usable, it is necessary to reduce hights of rays on a visual field direction changing prism which is to be disposed in the vicinity of the tip of the objective optical system. In order to reduce these hights of rays, it is necessary to locate the pupil of the objective optical system in the vicinity of the tip of the objective optical system.

Requirements for a pupil of the objective optical system are conflicting with each other as described above when a non-flexible endoscope for oblique observation which has a wide field angle and is practically usable is to be obtained. In order to meet the requirements which are conflicting with each other, it is indispensable to shorten a total length of the objective optical system and locate the pupil of the objective optical system in the vicinity of the tip of the objective optical system.

A total length of the objective optical system has been shortened to widen a field angle and a pupil of the objective optical system has been located in the vicinity of the tip of the objective optical system to obtain an optical system for non-flexible endoscopes for oblique observation which is practically usable.

The condition (1) is required to configure the optical system according to the present invention so that it has a wide field angle and is compatible with a non-flexible endoscope for oblique observation which is practically usable.

The condition (1) defines a ratio of a total length relative to an outside diameter of the objective optical system. If the ratio L/D1 has a value which is so large as to exceed the upper limit of 20 of the condition (1), it will be impossible to locate a pupil of the objective optical system in the vicinity of the tip of the objective optical system and enlarge angles of the rays coming from the marginal portions of the visual field relative to the optical axis at a location of the pupil of the objective optical system. Accordingly, it is impossible to obtain an optical system which has a wide field angle and is compatible with a non-flexible endoscope for oblique observation which is practically usable.

The optical system for non-flexible endoscopes according to the present invention which satisfies the condition (1) mentioned above has a wide field angle and is compatible with a non-flexible endoscope for oblique observation which is practically usable.

However, the observation optical system which is configured to satisfy the condition (1) has an NA smaller than that of the conventional optical system for non-flexible endoscoes having an outside diameter which is the same as that of the optical system satisfying the condition (1), whereby brightness is lower in the optical system satisfying the condition (1).

In order to solve the problem of this lower brightness, the optical system according to the present invention is configured to satisfy the condition (2).

Brightness of an optical system for non-flexible endoscopes which has an illumination optical system and an observation optical system is proportional to a product of brightness of the illumination optical system multiplied by brightness of the observation optical system. The brightness of the observation optical system is proportional to a product of a square of an NA multiplied by a square of an image height, and an NA and an image height are proportional to an outside diameter of the observation optical system. Accordingly, the brightness of the observation optical system is proportional to an outside diameter of the observation optical system raised to the fourth power.

Furthermore, the brightness of the illumination optical system is proportional to a square of an outside diameter of the illumination optical system when illuminance of rays incident on the illumination optical system is uniform.

On the basis of the points described above, it is general to determine maximum brightness of an optical system for non-flexible endoscopes by optimalizing outside diameters of an illumination optical system and an observing optical system which are to be disposed in an insert section.

When the illumination optical system has a large outside diameter, however, it is impossible to be optimum the outside diameter.

The illumination optical system condenses rays emitted from a light source to illuminate an object with the rays and an end surface of incidence of a non-flexible endoscopes is disposed at a location where the rays are condensed or a location equivalent thereto. When the illumination optical system of the non-flexible endoscope has an outside diameter which is large as compared with a spot of the condensed rays, however, illuminance of rays incident on the illumination optical system is ununiform and brightness of the illumination optical system is not proportional to a square of the outside diameter.

In such a case, brightness of the optical system for non-flexible endoscopes can be enhanced not by enlarging the outside diameter of the illumination optical system but by enlarging an outside diameter of the observation optical system.

Taking the points described above into consideration, the condition (2) has been adopted for normalizing outside diameters of the illumination optical system and the observation optical system.

The condition (2) defines a ratio D2/D3 between outside diameters of the relay optical system and the insert section. If the ratio D2/D3 is so high as to exceed the upper limit of 0.9 of the condition (2), the relay optical system will have a large outside diameter, thereby enlarging an NA of the observation optical system and brighten it. However, an illumination optical system which can be disposed in the insert section will be remarkably small and dark. As a result, the optical system for non-flexible endoscopes will undesirably be dark as a whole.

If the ratio D2/D3 is so low as to exceed the lower limit of 0.7 of the condition (2), more illumination optical systems can be disposed in the insert section, thereby brightening the illumination optical system. However, the illumination optical system cannot be brightened in proportion to a square of its outside diameter even when a ratio of the illumination optical system is further enhanced. Furthermore, an outside diameter of the relay optical system is reduced, whereby the observation optical system has a smaller NA and is darkened. As a result, the optical system for non-flexible endoscopes is darkened as a whole.

In order to configure the optical system for non-flexible endoscopes according to the present invention so as to have a large field angle, it is desirable to satisfy, in place of the condition (1), the following condition (1-1):

$$L/D1 < 12 \quad (1\text{-}1)$$

The condition (1-1) defines a range which is narrowed by modifying the upper limit of the condition (1). If the upper limit of 12 of the condition (1-1) is exceeded, certain specifications required for non-flexible endoscopes may make it impossible to meet all the requirements for an optical system which has a wide field angle, aberrations corrected sufficiently favorably and prevent rays from being eclipsed by a non-flexible endoscope for oblique observation.

In order to maintain sufficient brightness in the optical system for non-flexible endoscopes according to the present invention, it is more desirable to satisfy the following condition (3):

$$7 \text{ mm} < D3 < 15 \text{ mm} \quad (3)$$

The condition (3) defines an outside diameter of the insert section. If the outside diameter D3 of the insert section is so small as to exceed the lower limit of 7 mm of the condition (3), the optical system for non-flexible endoscopes may not maintain required brightness. If the outside diameter D3 of the insert section is so large as to exceed the upper limit of 15 mm of the condition (3), in contrast, it will be impossible to meet a requirement for less pains of patients during surgical operations under endoscopic observation though sufficient brightness can be maintained.

In order to maintain sufficient brightness in the optical system for non-flexible endoscopes, it is desirable to satisfy the following condition (4):

$$200 \text{ mm} < L12 < 450 \text{ mm} \quad (4)$$

wherein the reference symbol L12 represents a distance as measured from a tip of the objective optical system to a location of an image to be transferred by the relay optical system.

If the distance L12 is so long as to exceed the upper limit of 450 mm of the condition (4), the observation optical system will have an NA which is too small to maintain required brightness. If L12 has a value exceeding the lower limit of 200 mm of the condition (4), the distance L12 will be too short and the objective optical system may not be brought sufficiently close to an object to be observed in a cavity.

Now, the preferred embodiments of the optical system for non-flexible endoscopes according to the present invention will be described in a form of numerical data:

Embodiment 1 object distance = −65 mm, image height = 3.7 mm,
image side NA = 0.076, field angle = 80.0°,
outside diameter = 9 mm ($r_1$~$r_2$), 8.5 mm ($r_3$~$r_4$), 9.5 mm ($r_5$~$r_{30}$), 12.6 mm ($r_{32}$~$r_{34}$)

$r_1 = \infty$
  $d_1 = 0.7$   $n_1 = 1.7682$   $\nu_1 = 71.7$
$r_2 = \infty$
  $d_2 = 0.35$
$r_3 = \infty$
  $d_3 = 0.5$   $n_2 = 1.78472$   $\nu_2 = 25.76$
$r_4 = 3.7911$ (aspherical surface)
  $d_4 = 1.45$
$r_5 = \infty$
  $d_5 = 21.57$   $n_3 = 1.883$   $\nu_3 = 40.76$
$r_6 = \infty$
  $d_6 = 12.86$   $n_4 = 1.48749$   $\nu_4 = 70.23$
$r_7 = -15.26$
  $d_7 = 1$
$r_8 = 19.566$
  $d_8 = 9.46$   $n_5 = 1.48749$   $\nu_5 = 70.23$
$r_9 = -14.611$
  $d_9 = 1.5$   $n_6 = 1.84666$   $\nu_6 = 23.78$
$r_{10} = -24.4690$
  $d_{10} = 2$
$r_{11} = \infty$
  $d_{11} = 27.65$   $n_7 = 1.72916$   $\nu_7 = 54.68$
$r_{12} = -9.205$
  $d_{12} = 1.5$   $n_8 = 1.834$   $\nu_8 = 37.16$
$r_{13} = -33.158$
  $d_{13} = 1$
$r_{14} = 9.813$
  $d_{14} = 3.5$   $n_9 = 1.48749$   $\nu_9 = 70.23$
$r_{15} = -9.813$
  $d_{15} = 1.5$   $n_{10} = 1.84666$   $\nu_{10} = 23.78$
$r_{16} = 9.813$
  $d_{16} = 8.65$   $n_{11} = 1.72916$   $\nu_{11} = 54.68$
$r_{17} = \infty$ (image)
  $d_{17} = 8.65$   $n_{12} = 1.72916$   $\nu_{12} = 54.68$
$r_{18} = \infty$
  $d_{18} = 2$
$r_{19} = 38.839$
  $d_{19} = 45$   $n_{13} = 1.6228$   $\nu_{13} = 57.05$
$r_{20} = \infty$
  $d_{20} = 2$
$r_{21} = \infty$
  $d_{21} = 40.5$   $n_{14} = 1.6228$   $\nu_{14} = 57.05$
$r_{22} = -13.342$
  $d_{22} = 2$   $n_{15} = 1.883$   $\nu_{15} = 40.76$
$r_{23} = -51.606$
  $d_{23} = 1.5$
$r_{24} = 35.607$
  $d_{24} = 16$   $n_{16} = 1.5927$   $\nu_{16} = 35.31$
$r_{25} = -35.607$
  $d_{25} = 1.5$
$r_{26} = 51.606$
  $d_{26} = 2$   $n_{17} = 1.883$   $\nu_{17} = 40.76$
$r_{27} = 13.342$
  $d_{27} = 40.5$   $n_{18} = 1.6228$   $\nu_{18} = 57.05$
$r_{28} = \infty$
  $d_{28} = 2$
$r_{29} = \infty$
  $d_{29} = 45$   $n_{19} = 1.6228$   $\nu_{19} = 57.05$
$r_{30} = -38.839$
  $d_{30} = 7.0004$
$r_{31} = \infty$ (image)
  $d_{31} = 27.77$
$r_{32} = 34.013$
  $d_{32} = 2$   $n_{20} = 1.84666$   $\nu_{20} = 23.78$
$r_{33} = 11.838$
  $d_{33} = 5$   $n_{21} = 1.762$   $\nu_{21} = 40.1$
$r_{34} = -46.993$ aspherical surface coefficients
K = −1.0128, F = −5.0000 × $10^{-6}$, G = −5.0000 × $10^{-7}$
L = 95.19 mm, L12 = 310.8404 mm, D1 = 9.5 mm,
D2 = 9.5 mm, D3 = 12 mm, L/D1 = 10.02, D2/D3 = 0.79.

Embodiment 2 object distance = −30 mm, image height = 3.15 mm,
image side NA = 0.045, field angle = 80.0°,
outside diameter = 8.2 mm ($r_1 \sim r_{28}$)

$r_1 = \infty$
    $d_1 = 0.7$      $n_1 = 1.769$      $\nu_1 = 64.15$
$r_2 = \infty$
    $d_2 = 1.1$
$r_3 = \infty$
    $d_3 = 1.6$      $n_2 = 1.78472$      $\nu_2 = 25.76$
$r_4 = 3.8489$
    $d_4 = 1.1086$
$r_5 = \infty$
    $d_5 = 12.9$      $n_3 = 1.8061$      $\nu_3 = 40.92$
$r_6 = -7.1565$
    $d_6 = 0.5$
$r_7 = 18.0015$
    $d_7 = 5.8$      $n_4 = 1.58313$      $\nu_4 = 59.38$
$r_8 = -5.3$
    $d_8 = 1.1$      $n_5 = 1.84666$      $\nu_5 = 23.78$
$r_9 = \infty$
    $d_9 = 1.1457$
$r_{10} = 7.1293$
    $d_{10} = 4.53$      $n_6 = 1.51633$      $\nu_6 = 64.14$
$r_{11} = -7.1293$
    $d_{11} = 2.5$      $n_7 = 1.71999$      $\nu_7 = 50.25$
$r_{12} = -36.4579$
    $d_{12} = 5.1711$
$r_{13} = \infty$ (image)
    $d_{13} = 7$
$r_{14} = 43.0763$
    $d_{14} = 34.0161$      $n_8 = 1.48749$      $\nu_8 = 70.23$
$r_{15} = \infty$
    $d_{15} = 2$
$r_{16} = \infty$
    $d_{16} = 50$      $n_9 = 1.72916$      $\nu_9 = 54.68$
$r_{17} = \infty$
    $d_{17} = 2$
$r_{18} = \infty$
    $d_{18} = 50$      $n_{10} = 1.72916$      $\nu_{10} = 54.68$
$r_{19} = \infty$
    $d_{19} = 1.0372$
$r_{20} = 45.1888$
    $d_{20} = 5.74$      $n_{11} = 1.58913$      $\nu_{11} = 61.14$
$r_{21} = -18.7595$
    $d_{21} = 2$      $n_{12} = 1.8044$      $\nu_{12} = 39.59$
$r_{22} = -40.7567$
    $d_{22} = 1.1907$
$r_{23} = \infty$
    $d_{23} = 50$      $n_{13} = 1.72916$      $\nu_{13} = 54.68$
$r_{24} = \infty$
    $d_{24} = 2$
$r_{25} = \infty$
    $d_{25} = 50$      $n_{14} = 1.72916$      $\nu_{14} = 54.68$
$r_{26} = \infty$
    $d_{26} = 2$
$r_{27} = \infty$
    $d_{27} = 34.0161$      $n_{15} = 1.48749$      $\nu_{15} = 70.23$
$r_{28} = -43.0763$
    $d_{28} = 6.9999$
$r_{29} = \infty$ (image)
L = 37.1554 mm, L12 = 337.1554 mm, D1 = 8.2 mm,
D2 = 8.2 mm, D3 = 10 mm, L/D1 = 4.53, D2/D3 = 0.82 wherein the reference symbols $r_1$, $r_2$, . . . represent radii of curvature on surfaces of respective lens elements, the reference symbols $d_1$, $d_2$, . . . designate thicknesses of the respective lens elements and airspaces reserved therebetween, the reference symbols $n_1$, $n_2$, . . . denote refractive indices of the respective lens elements, and the reference symbols $\nu_1$, $\nu_2$, . . . represent Abbe's numbers of the respective lens elements.

Figure 3:
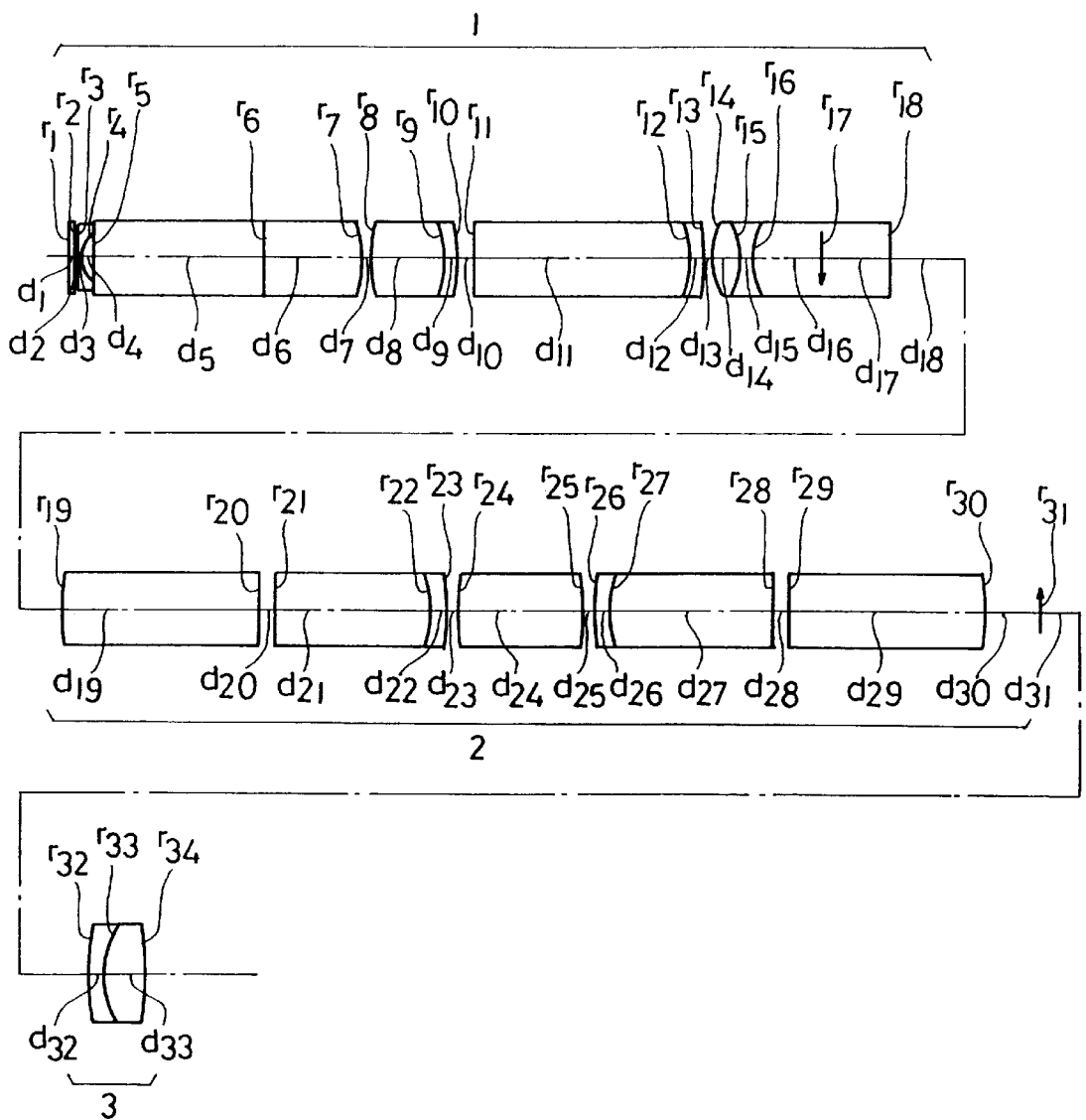
FIG. 3 shows a sectional view illustrating a composition of a first embodiment of an optical system to be used in the non-flexible endoscope according to the present invention.

The first embodiment has a composition illustrated in FIG. 3, wherein a reference numeral 1 represents an objective optical system ($r_1$ through $r_{18}$), a reference numeral 2 designates a relay optical system ($r_{19}$ through $r_{30}$) and a reference numeral 3 denotes an eyepiece system ($r_{32}$ through $r_{34}$). Out of these optical systems, the objective optical system 1 and the relay optical system 2 are disposed in an insert section, whereas the eyepiece system 3 is disposed outside the insert section.

In the first embodiment, the reference symbols $r_{17}$ and $r_{31}$ represent locations of images, out of which ($r_{31}$) is an erect image. Furthermore, an imaginary stop is disposed at a location of an optical path length of 20.9409 mm as measured on the image side from the surface $r_5$.

Figure 4A:
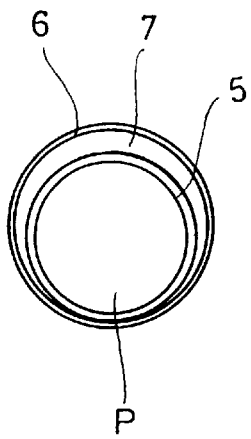
FIGS. 4A and 4B respectively show a front view and a sectional view illustrating a tip of a non-flexible endoscope comprising the optical system preferred as the first embodiment.
Figure 4B:
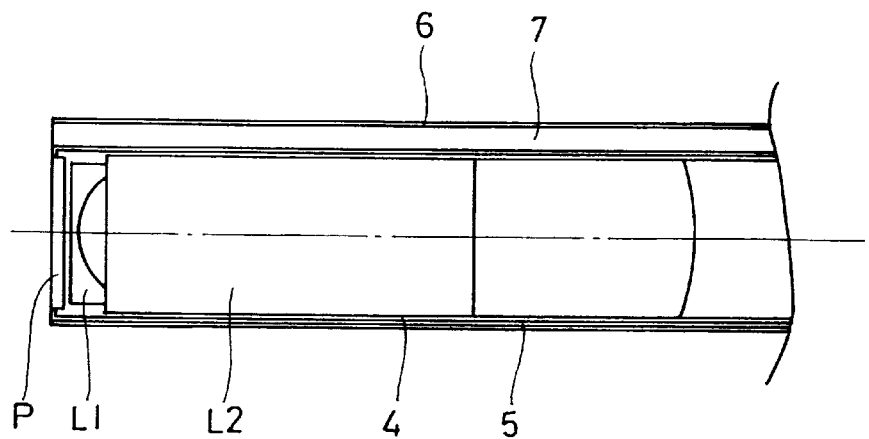

FIGS. 4A and 4B shows a composition of a tip of the optical system for non-flexible endoscopes preferred as the first embodiment: FIG. 4A being a front view and FIG. 4B being a sectional view.

The lens components ($r_5$ through $r_{18}$) of the objective optical system, except a plane parallel plate P and a plano concave lens component L1 which are disposed on the object side, and the lens components ($r_{19} \sim r_{30}$) of the relay optical system have an outside diameter of 9.5 mm. These lens components are disposed in a pipe 4 having an inside diameter of 9.5 mm with spacers interposed to determine intervals among the lens components. The plane parallel plate P disposed on a side of a tip of the objective optical system is cemented to a pipe 5 which is disposed outside the pipe 4 and the plano-concave lens component L1 is cemented to a planoconcave lens unit L2. Furthermore, an illumination optical system is disposed in a lunette space between a pipe 5 and a pipe 6 having an outside diameter of 12 mm.

The optical system preferred as the first embodiment satisfies the conditions (1) and (2). The objective optical system comprises a plano-concave aspherical surface to correct distortion.

When a direction along an optical system is taken as z and a direction perpendicular to the optical axis is taken as y, a shape of the aspherical surface of the first embodiment is expressed by the following formula:

$$z(y^2/r)/[1+\{1-(k+1)(y/r)^2\}^{1/12}]+Fy^6+Gy^8$$

Furthermore, airspaces ($d_{20}$ and $d_{28}$) are reserved in the relay lens system to shorten rod lens components, thereby preventing the rod lens components from being broken in practical use. From a viewpoint of optical performance, these rod lens components may be integrated with one another by filling the airspaces before and after the rod lens components with glass with an optical path length kept unchanged or by cementing the rod lens components to one another after changing their thicknesses with the optical path length kept unchanged.

Figure 5A:
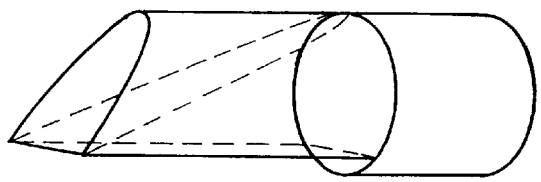
FIGS. 5A through 5C show diagrams illustrating a tip of a non-flexible endoscope for oblique observation comprising the optical system preferred as the first embodiment, FIG. 5A being a perspective view of a prism, FIG. 5b being a front view of a non-flexible endoscope for oblique observation, and FIG. 5C being a sectional view of the non-flexible endoscope for oblique observation.
Figure 5B:
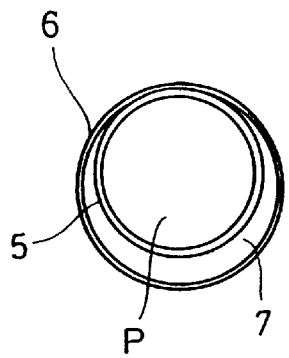
Figure 5C:
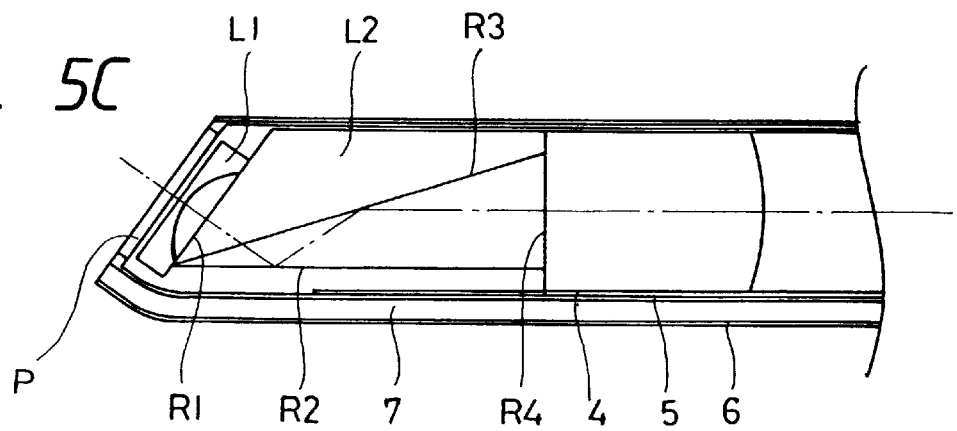

Furthermore, the optical system preferred as the first embodiment can be configured as one for an non-flexible endoscope for oblique observation by configuring the rod lens component ($r_5$ to $r_6$) as a visual field direction changing prism. FIGS. 5A, 5B and 5C show a composition of the visual field direction changing prism in the first embodiment: FIG. 5A being a perspective view of the prism, FIG. 5B being a front view of a non-flexible endoscope for oblique observation, and FIG. 5C being a sectional view of the non-flexible endoscope for oblique observation.

When this visual field direction changing prism is used, an optical axis of the relay optical system can be inclined at an angle of 35°. This visual field direction changing prism comprises, in order from the object side, a surface of incidence R1 which is perpendicular to an optical axis on the object side, a first reflecting surface R2 which is in parallel with an optical axis of the relay optical system, a second reflecting surface R3 which is inclined relative to the first reflecting surface at an angle of 17.5°, or half the visual field direction changing angle of 35° and a surface of emergence R4 which is perpendicular to the optical axis of the relay optical system. Furthermore, both the first reflecting surface R2 and the second reflecting surface R3 utilize total reflection. In order to reserve margins for critical angles of these totally reflecting surfaces, it is desirable to use a material which has a high refractive index for the prism.

The visual field direction changing prism used in the first embodiment is configured to have an optical path length of 21.57 mm between the surface of incidence R1 and the surface of emergence R4, whereby a light bundle within a visual field is not eclipsed by the surfaces and the prism is usable for a non-flexible endoscope for oblique observation.

Even in the non-flexible endoscope for oblique observation preferred as the first embodiment wherein the visual field direction changing prism is used in the tip of the optical system for non-flexible endoscopes, less components of the observation optical system are disposed in a pipe 4 having an inside diameter of 9.5 mm with spacers interposed to determine spacings as described above. Furthermore, a plane parallel plate P on a side of a tip of the objective optical system is cemented to a pipe 5 which is disposed outside the pipe 4 and a plano-concave lens component L1 is cemented to a visual field direction changing unit L2 after adjustment.

Furthermore, an illumination optical system is disposed in a lunette space 7 between the pipe 5 and a pipe 6 having an outside diameter of 12 mm to illuminate the visual field direction. For this purpose, an illumination optical system 13 is disposed as shown in FIG. 5C.

Figure 6:
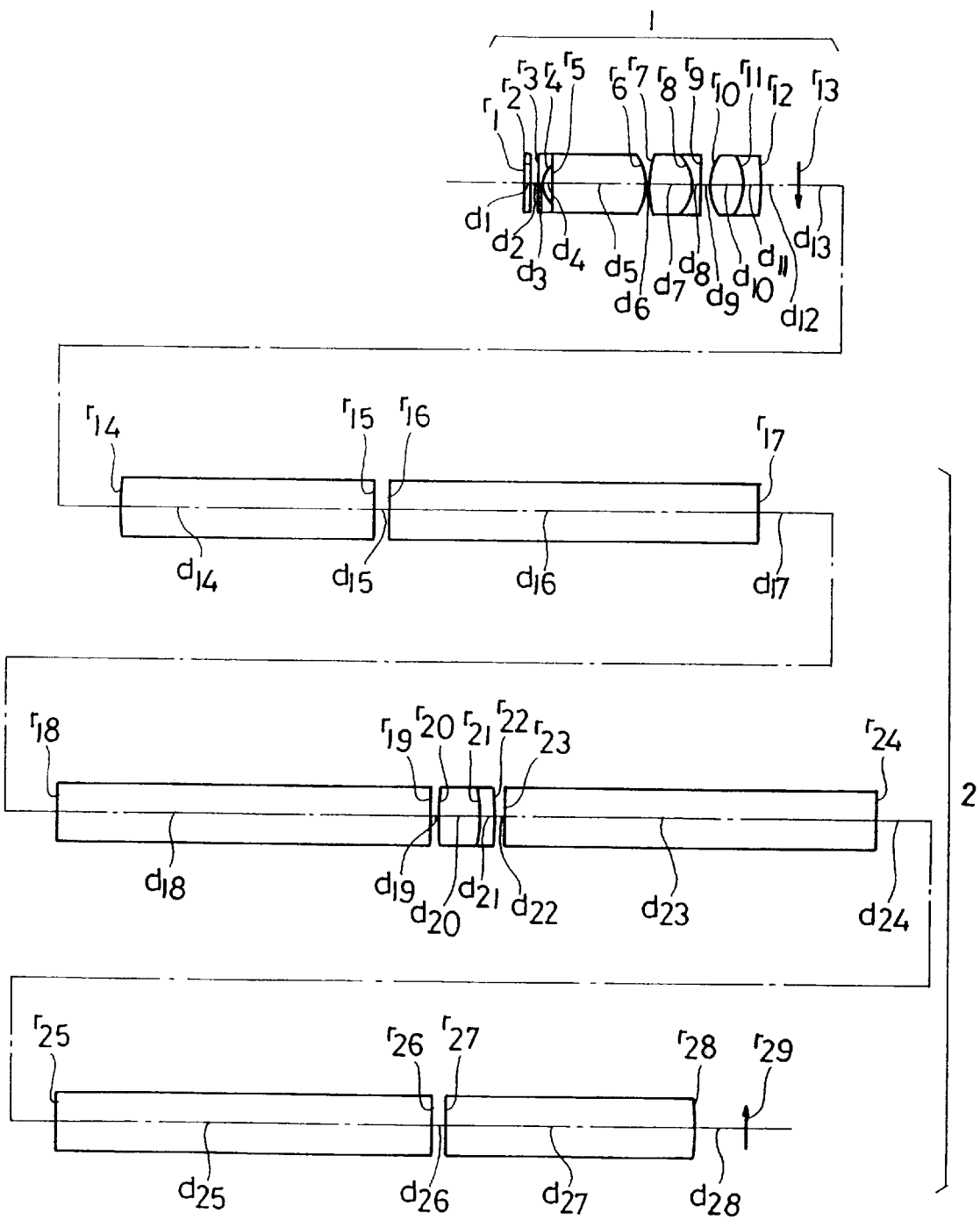
FIG. 6 shows a sectional view illustrating a composition of a second embodiment of the optical system to be used in the non-flexible endoscope according to the present invention.

The second embodiment has a composition illustrated in FIG. 6, wherein an objective optical system 1 ($r_1$ through $r_{12}$) and a relay optical system ($r_{14}$ through $r_{28}$) of an observation optical system which are to be disposed in an insert section are shown. Reference symbols $r_{13}$ and $r_{29}$ represent locations of images, out of which $r_{29}$ is an erect image. Furthermore, an imaginary stop is disposed at a location which has an optical path length of 3.7192 mm as measured from the surface $r_5$ toward the image side.

The second embodiment satisfies the conditions (1) and (2). Furthermore, the airspaces ($d_{15}$, $d_{17}$, $d_{24}$ and $d_{26}$) are reserved to shorten the rod lens components, thereby preventing breakage of these lens components as in the first embodiment.

As already described with reference to the first embodiment, it is possible to fill the airspaces before and after the rod lens components with glass without changing an optical path length or integrate the rod lens components to one another after changing their thicknesses.

Furthermore, the second embodiment uses a visual field direction changing prism shown in FIG. 7 which is capable of inclining a visual field direction at an angle of 30° relative to an optical axis of the relay optical system.

The visual field direction changing prism comprises, in order from the object side, a surface of incidence R1 which is perpendicular to an optical axis on the object side, a second reflecting surface R2 which is inclined 30° relative to an optical axis of the relay optical system, a third reflecting surface R3 which is inclined 45° relative to the optical axis of the relay optical system and a surface of emergence R4 which is perpendicular to the optical axis of the relay optical system. Out of these surfaces, both the reflecting surfaces R2 and R3 utilize reflection by metal films.

The present invention makes it possible to obtain an optical system for non-flexible endoscopes which is composed of lens components in a number reduced by selecting a single image relay cycle, and compatible with non-flexible endoscopes for oblique observation which provide high quality images, have wide field angles and are practically usable.

I claim:

1. An optical system for non-flexible endoscopes comprising: an illumination optical system and an observation optical system which are disposed in an insert section, wherein said observation optical system comprises, in order from a side of a tip, at least an objective optical system and a single relay cycle type relay optical system, and satisfies the following conditions (1) and (2):

$$L/D1 < 20 \tag{1}$$

$$0.7 < D2/D3 < 0.9 \tag{2}$$

wherein the reference symbol L represents a distance as measured from a tip of the objective optical system to an image formed by the objective optical system, the reference symbol D1 designates an outside diameter of a lens component in the objective optical system whichever has a largest outside diameter, the reference symbol D2 denotes an outside diameter of a lens component in the relay optical system whichever has a largest outside diameter and the reference symbol D3 represents an outside diameter of the insert section.

2. An endoscope according to claim 1 satisfying, in place of the condition (1), the following condition (1-1):

$$L/D1 < 12 \tag{1-1}$$

3. An optical system for non-flexible endoscope according to claim 1 or 2 satisfying the following condition (3):

$$7 \text{ mm} < D3 < 15 \text{ mm} \tag{3}$$

4. An optical system for non-flexible endoscopes according to claim 1 or 2 satisfying the following condition (4);

$$200 \text{ mm} < L12 < 450 \text{ mm} \tag{4}$$

wherein the reference symbol L12 represents a distance as measured from the tip of the objective optical system to an image transferred by the relay optical system.

5. An optical system for non-flexible endoscopes according to claim 3 satisfying the following condition (4):

$$200 \text{ mm} < L12 < 450 \text{ mm} \tag{4}$$

wherein the reference symbol L12 represents a distance as measured from the tip of the objective optical system to an image transferred by the relay optical system.

* * * * *